United States Patent [19]

Haber et al.

[11] Patent Number: 5,312,336

[45] Date of Patent: May 17, 1994

[54] COMPONENT MIXING SYRINGE

[75] Inventors: Terry M. Haber, Lake Forest; William H. Smedley, Lake Elsinore; Clark B. Foster, Laguna Niguel, all of Calif.

[73] Assignee: Habley Medical Technology Corporation, Laguna Hills, Calif.

[21] Appl. No.: 47,125

[22] Filed: Apr. 14, 1993

[51] Int. Cl.$^5$ ...................... A61M 37/00; A61M 5/00
[52] U.S. Cl. ........................................ 604/89; 604/90; 604/92; 604/191
[58] Field of Search ........................... 604/82–84, 604/89, 90, 92, 191, 416, 212–214, 85–88, 91; 206/219, 221

[56] References Cited

U.S. PATENT DOCUMENTS

| | | | |
|---|---|---|---|
| 212,046 | 2/1879 | Palmer | 604/191 X |
| 553,234 | 1/1896 | Finot | 604/191 X |
| 1,234,582 | 7/1917 | Trueblood | 604/191 X |
| 2,591,706 | 4/1952 | Lockhart | 604/90 X |
| 3,052,240 | 9/1962 | Silver et al. | 604/89 X |
| 3,749,084 | 7/1973 | Cucchiara | 604/191 X |
| 4,185,628 | 1/1980 | Kopfer | 604/89 X |
| 4,886,495 | 12/1989 | Reynolds | 604/191 X |
| 4,898,580 | 2/1990 | Crowley | 604/90 |
| 5,158,546 | 10/1992 | Haber et al. | 604/89 X |
| 5,220,948 | 6/1993 | Haber et al. | 604/90 X |

Primary Examiner—C. Fred Rosenbaum
Assistant Examiner—Frank Wilkens, III
Attorney, Agent, or Firm—Townsend and Townsend Khourie and Crew

[57] ABSTRACT

A two component mixing syringe for mixing and then self-administering a pharmaceutical by injection. A first liquid component is contained within an annular volume between a pair of coaxial housings. A pair of sealing bands defines the upper and lower boundaries of the annular volume. The lower sealing band is located above an aperture communicating with the inner housing interior. A driving sleeve is mounted with a driving end resting on the upper sealing band, the sleeve being located in the annular space between the two housings. Downward motion of the sleeve forces the upper sealing band downwardly causing the liquid component to drive the lower seal downwards past the cross bore. Thereafter, the liquid is free to flow through the cross bore and mix with the second component in the interior of the inner housing element.

9 Claims, 9 Drawing Sheets

COMPONENT MIXING SYRINGE

BACKGROUND OF THE INVENTION

This invention relates to pharmaceutical containers of the two component mixing type having an attachable syringe needle.

Many pharmaceuticals have extremely limited shelf life and thus must be stored as two separate components. Just prior to use, the container is manipulated in such a manner that the individual components are mixed together to activate the pharmaceutical. Many such containers are also provided with an attachable cap having a double ended syringe needle which penetrates a septum when the cap is installed on the outlet end of the container. Such containers are also typically provided with a plunger which permit the mixed pharmaceutical to be expelled through the needle for injection by the user. When the pharmaceutical is intended to be self-administered by the patient, it is necessary that the mixing operation be simple and reliable in order to ensure that the components are thoroughly admixed in a relatively foolproof fashion. Such containers must also ensure that the two components cannot inadvertently mix during storage of the container.

Some two component pharmaceuticals such as the large protein type medications, typically used to treat ulcers, low red blood cell count, hepatitis C and some types of cancer, are available in a package including a tray, a vial containing the dry component, a vial containing the liquid component and a syringe. In use, the patient inserts the syringe into the liquid component vial, withdraws the liquid component and injects it into the dry component vial. Thereafter, the patient withdraws a unit dosage for injection. For a single dosage package, the entire collection of components is then disposed of. For a multiple usage package, the mixture in the vial is preserved for subsequent self-administration. This arrangement is somewhat cumbersome and inconvenient to use, particularly when self-administered by the patient.

SUMMARY OF THE INVENTION

The invention comprises a component mixing syringe capable of containing in separated condition a liquid component and a second component during shipment and storage and affording relatively simple operation when mixing the two components prior to injection.

A first housing has a seal end and a second end remote from the seal end. A second housing is received within the first housing in such a manner as to form an annular space therewith, the second housing having a first end in sealing engagement with the seal end of the first housing and a second end. A septum is located within the first housing at the seal end thereof and is preferably captured between the seal end of the first housing and the first end of the second housing. The seal end of the first housing is preferably provided with an externally threaded portion for removably receiving a syringe needle/cap assembly. The second housing is provided with at least one aperture extending therethrough the housing wall adjacent the first end to provide fluid communication between the annular volume and the interior of the second housing. First and second sealing bands are slidably received about the second housing and are mutually spaced therealong, with both of the sealing bands being initially positioned above the aperture to form a sealed annular volume for the first liquid component. The sealing bands may comprise O rings or bands having a rectangular cross-section.

A band driving sleeve is slidably received about the second housing and is initially located partially within the first housing, the band driving sleeve having a first end positioned adjacent the upper one of the mutually spaced bands and a second end.

A plunger having a seal end received within the second housing forms an enclosed volume for the second component.

The invention further includes means for enabling the band driving sleeve to be translated toward the seal end of the first housing to drive the upper one of the mutually spaced sealing bands toward the aperture. When the first liquid component is contained within the annular volume, translation of the upper sealing band towards the aperture causes the first liquid component to force the lower one of the sealing bands to slide below the aperture through the second housing and permit the first liquid component to flow thru the aperture and mix with the second component within the interior of the second housing.

In one embodiment, the enabling means comprises a driving member slidably received about the first housing and having a first portion coupled to the band driving sleeve and a second end, the second end of the driving member being initially axially spaced from the seal end of the first housing and engageable therewith after a selected amount of axial travel to provide a limit stop. In a second embodiment, the enabling means comprises a shield member disposed about the first housing and secured thereto, the shield member having a grasping ledge formed along the periphery thereof to promote manual translation of the band driving sleeve axially of the first housing toward the seal end.

In order to lock the band driving sleeve in the extreme position after the first fluid component has been driven into the second component chamber, the band driving sleeve and the first housing are provided with complementary detent portions which engage when the band driving sleeve has been translated by a predetermined axial amount. The complementary detent portions preferably include at least one slot formed adjacent the second end of the first housing and an associated hook or pin formed adjacent the second end of the band driving sleeve.

For a fuller understanding of the nature and advantages of the invention, reference should be had to the ensuing detailed description taken in conjunction with the accompanying drawings.

DESCRIPTION OF THE PREFERRED EMBODIMENTS

Figure 1:
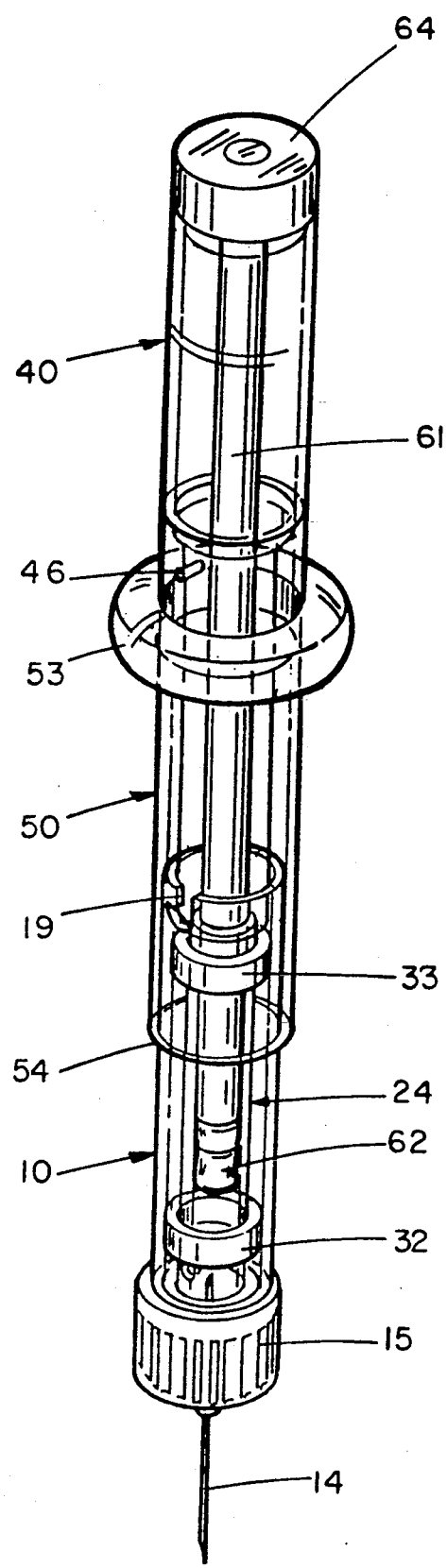
FIG. 1 is a perspective view illustrating a first embodiment of the invention in the fully assembled position prior to mixing of the two components.
Figure 2:
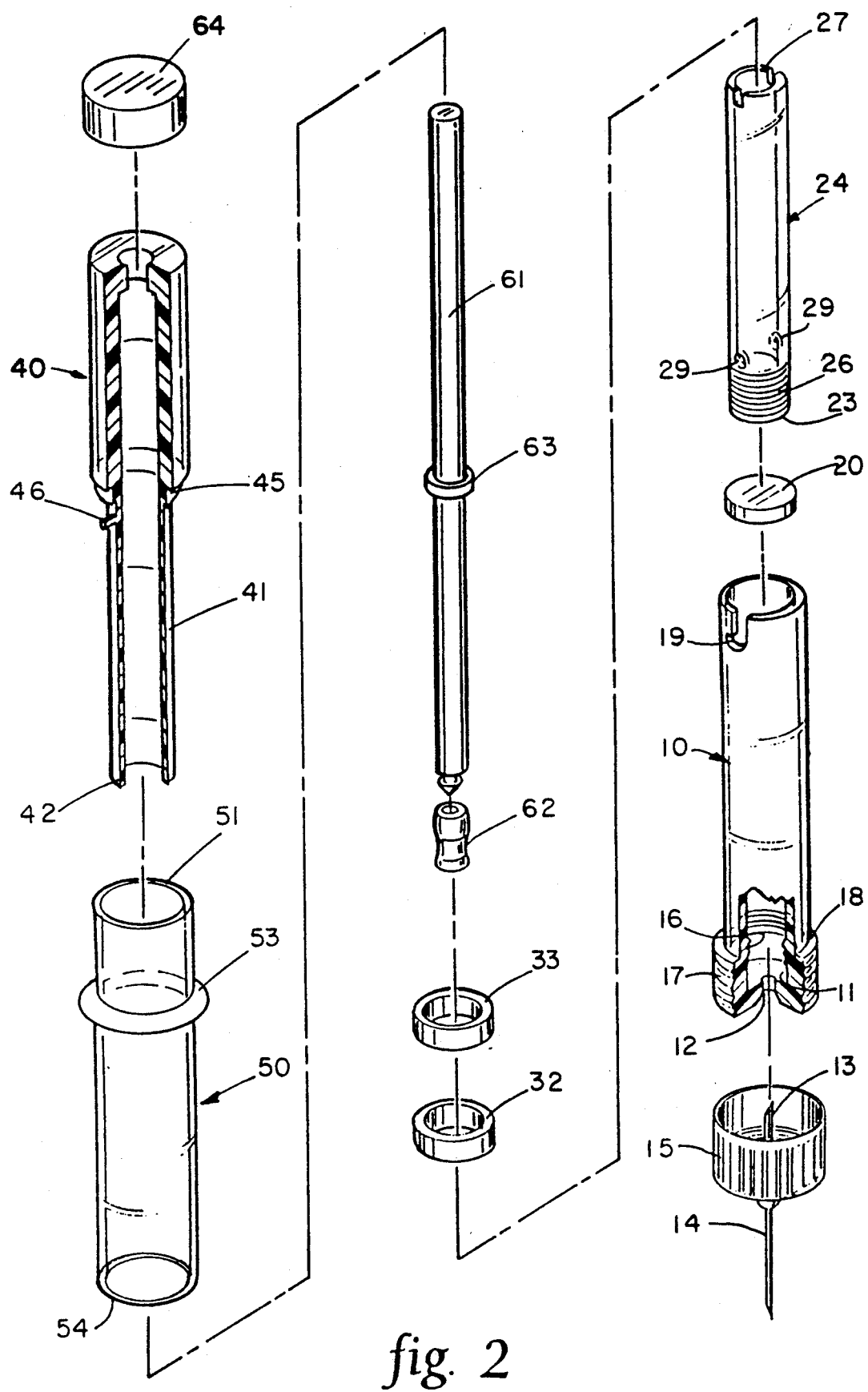
FIG. 2 is an exploded view, partially broken away, of the embodiment of FIG. 1.

Turning to the drawings, FIGS. 1-3A-3C illustrate a first embodiment of the invention designed for use as a single dose syringe. As seen in these Figs., a first housing 10 has a seal end 11 provided with a central aperture 12 for admitting one end 13 of a syringe needle 14 mounted in an attachable cap 15. Seal end 11 terminates in an externally threaded portion 17 having an abutment edge 18 for a purpose to be described. A septum 20 rests on the inside bottom of the sealing end 11 and is held in place by the lower end 23 of a second housing 24. End 23 is provided with an externally threaded portion 26 which is threadably engageable with an internally threaded portion 16 of first housing 10. By threading second housing 24 into first housing 10, septum 20 is captured therebetween. In addition, an annular space is formed due to the different dimensions of the outer diameter of second housing 24 and the inner diameter of first housing 10. To facilitate the insertion of second housing 24 into first housing 10, the upper end 27 of second housing 24 is notched as shown.

Second housing 24 is also provided with a pair of cross-flow apertures 29 formed through the wall structure thereof adjacent the lower end 23 just above the externally threaded portion 26.

A pair of sealing bands 32, 33 are arranged about the outer surface of second housing 24. Bands 32, 33 have a rectangular cross section and may be fabricated from any suitable material which is inert and non-reactive with a first liquid component. Sealing bands 32, 33 are initially installed in such a manner that both bands lie above apertures 29 and are spaced by an amount which will provide the requisite annular volume for the first liquid component, it being understood that the outer surfaces of bands 32, 33 sealingly engage the inner wall surface of first housing 10 as well as the outer wall surface of second housing 24.

A band driving sleeve generally designated with reference numeral 40 has a lower portion 41 dimensioned to be received within the annular space between first and second housings 10, 24 with the lower end 42 of band driving sleeve 40 in resting engagement on the top of upper sealing band 33. The upper portion of sleeve 40 has an enlarged region with a stepped intermediate portion 45. The outer diameter of stepped portion 45 is dimensioned to receive the upper end 51 of a driving member generally designated with reference numeral 50. Driving member 50 is secured to sleeve 40 in this embodiment, preferably by employing a suitable adhesive or thermally bonding upper end 51 along stepped intermediate portion 45. Driving member 50 is provided with a peripheral ledge 53 positioned at a convenient location along the length of driving member 50.

A plunger assembly includes a central rod 61 having a piston seal 62 secured to the lower end thereof in any suitable fashion, such as the press fit illustrated. The shaft of rod 61 is slidably received within the central hollow portion of sleeve 40 and extends outwardly thereof. A cap 64 is secured to the upper end of plunger rod 61.

In order to provide a locking detent mechanism for sleeve 40 and first housing 10, first housing 10 is provided with a pair of J slots 19; and sleeve 40 is provided with a pin 46. Slots 19 and pin 46 are dimensioned and relatively configured such that mutual engagement can be achieved when sleeve 40 has been driven to the lower extremity in the manner described below and rotated with respect to first housing 10.

In use, the first and second housings 10, 24 are secured together with septum 20 positioned therebetween and band 32 installed on second housing 24 at a location above aperture 29. The second pharmaceutical component 71 (see FIG. 3A) is then inserted within second housing 24. The first liquid component 70 is then poured into the annular space between housings 10 and 24, and second band 33 is installed. Thereafter, the plunger assembly is inserted within second housing 24, and the combined assembly of sleeve 40 and driving member 50 is manipulated over the top end of plunger rod 61 and moved downwardly until the lower edge 42 of sleeve 40 rests on the upper edge of upper sealing band 33. Thereafter, cap 64 is attached to the top end of plunger 61.

The assembled and loaded mixing syringe is then placed in a shipping container along with syringe cap 15. So long as the device remains in storage in the package, the two components remain separated by virtue of the seal provided by band 32.

Figure 3A:
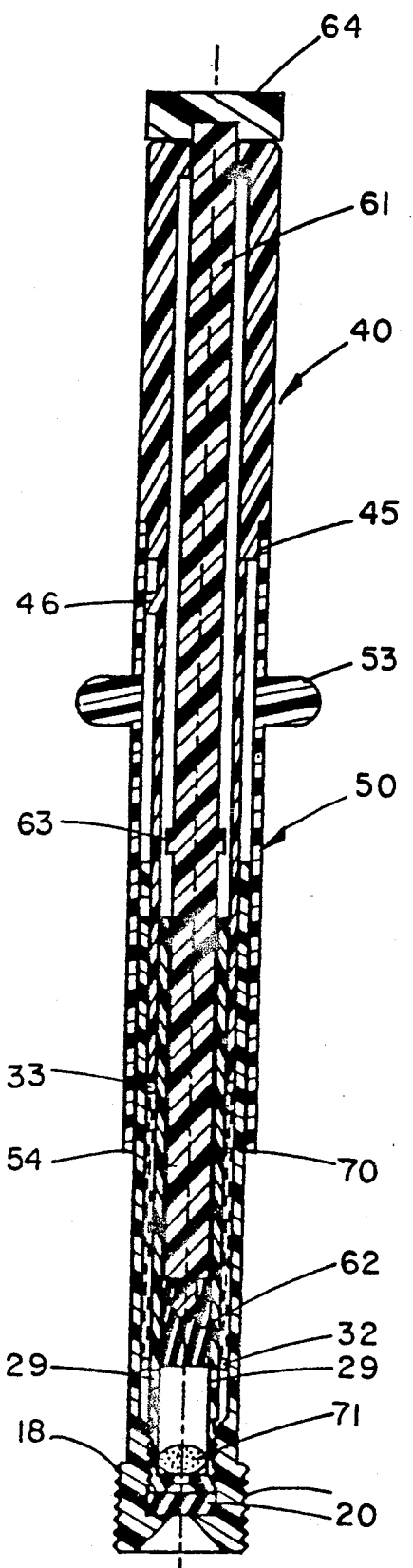
FIGS. 3A and 3B are full sectional views illustrating the FIG. 1 embodiment prior to mixing and after mixing.
Figure 3B:
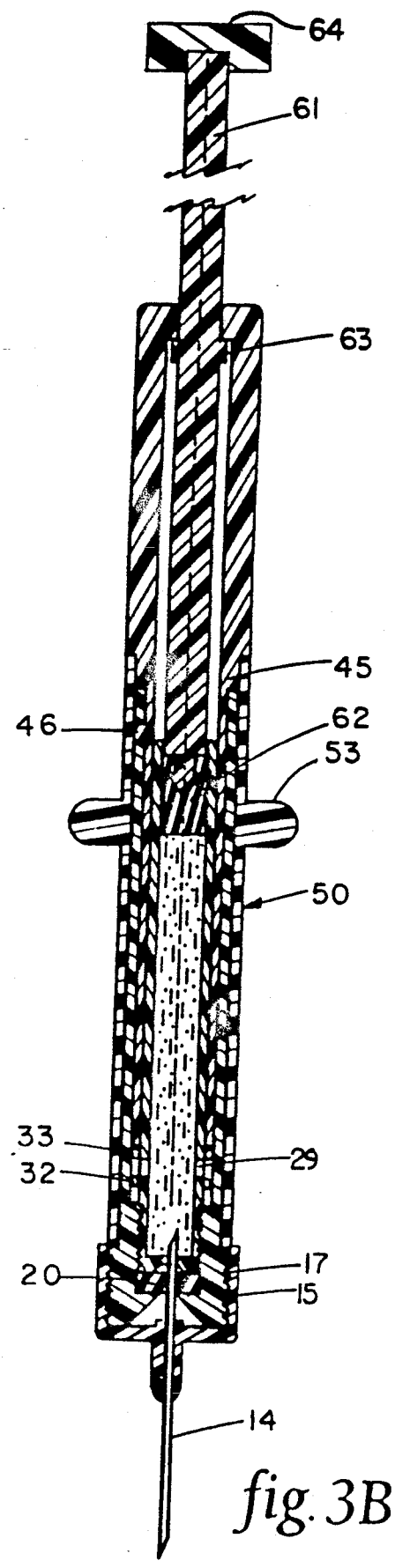
Figure 3C:
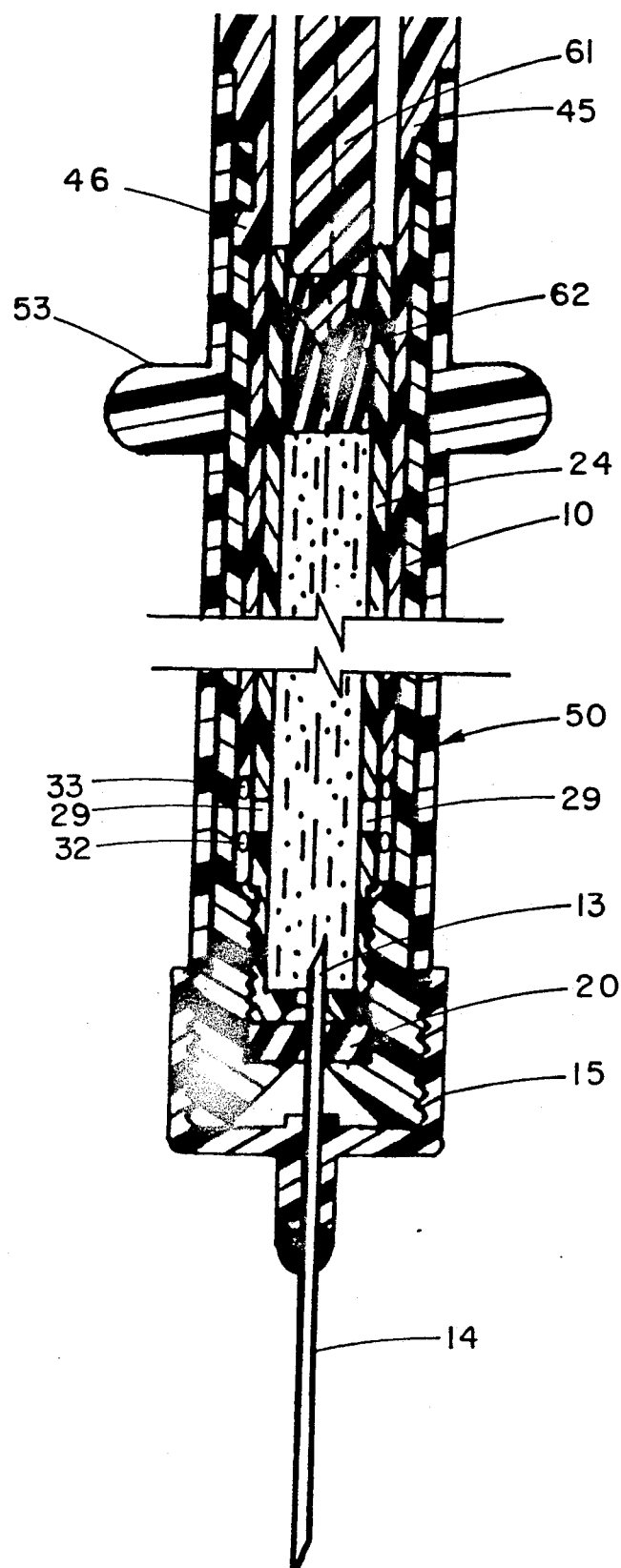
FIG. 3C is an enlarged sectional view illustrating the locking detent and the final position of the sealing bands.
Figure 4:
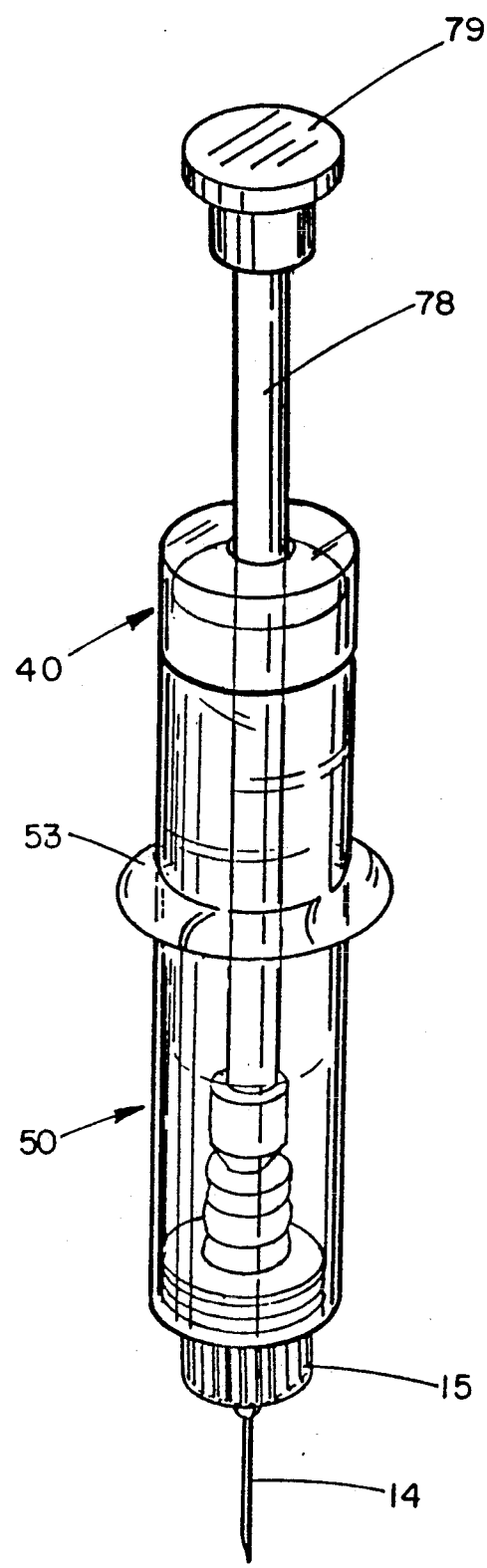
FIG. 4 is a perspective view of a second embodiment of the invention after mixing.
Figure 5:
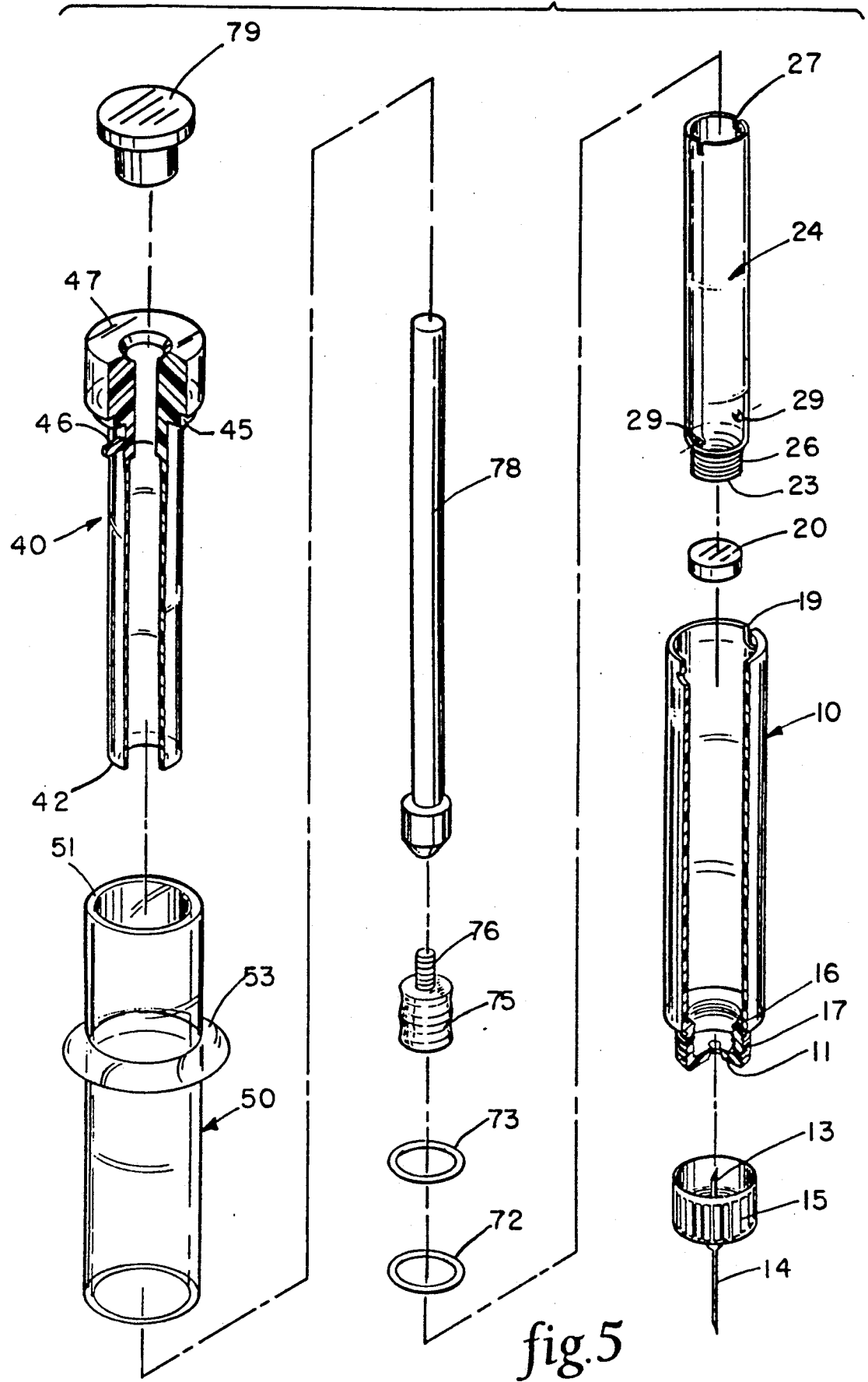
FIG. 5 is an exploded perspective view, partially broken away, of the embodiment of FIG. 4.

To mix the two components, driving member 50 is grasped by the ledge 53 and forced downwardly toward seal end 11 of first housing 10. Since driving member and sleeve 40 are bonded together, sleeve 40 is driven downwardly. The contact between lower end 42 of sleeve 40 and the upper surface of upper sealing band 33 causes the sealing band 33 to be driven downwardly between the outer surface of second housing 24 and the inner surface of first housing 10. This motion is transferred through the first liquid component to the lower sealing band 32, driving this member downwardly until band 32 clears the apertures 29. Thereafter, continued downward motion of the upper sealing band 33 in response to motion of sleeve 40 forces the first liquid component through apertures 29 and into the first component chamber, thereby thoroughly admixing the two components (FIG. 3B). As the liquid component flows into the interior of second housing element 24, the piston assembly is free to translate upwardly in response to the increased pressure. When sleeve 40 has been translated the maximum distance, the lower end 54 of driving member 50 engages the abutment surface 18 at the seal end of first housing 10, thereby preventing any further axial motion. Thereafter, the user may grasp the outer surface of sleeve 40 and end 11 of first housing 10 and rotate the pin 46 into the slot 19. Next, the cap 15 is installed on the externally threaded portion 17 of first housing 10, which causes the end 13 of needle 14 to penetrate septum 20 and become immersed in the pharmaceutical. The now mixed pharmaceutical may be injected by the patient (or an attending physician) by grasping driving member 50 adjacent ledge 53 and pressing on cap 64 of the plunger assembly.

FIGS. 4-6A-D illustrate a second embodiment of the invention suitable for use as either a single dose or multiple doses. As will be appreciated by those skilled in the art, after mixture the two component pharmaceutical will have limited effective lifetime typically measured in a few days and of sufficient time to permit the administration of successive doses at the prescribed interval.

In the embodiment of FIGS. 4–6A–6D, the same elements are given identical reference numerals to the corresponding elements in the first embodiment already described. The major difference between the structure and function of the two embodiments is as follows. In the second embodiment, driving member 50 is attached to first housing 10 by bonding with an adhesive or the equivalent. The seal end 11 of first housing 10 has a threaded portion 17 of reduced outer diameter since the abutment edge 18 is no longer required in this embodiment. The lower end of second housing 24 has a threaded portion 26 of similarly reduced diameter. Sealing bands 32, 33 are replaced by O rings 72, 73, which function in the same manner. The plunger assembly is provided with a piston seal 75 having a threaded extension 76 threadably received within a bore formed in the lower end of piston rod 78.

Figures 6A, 6B:
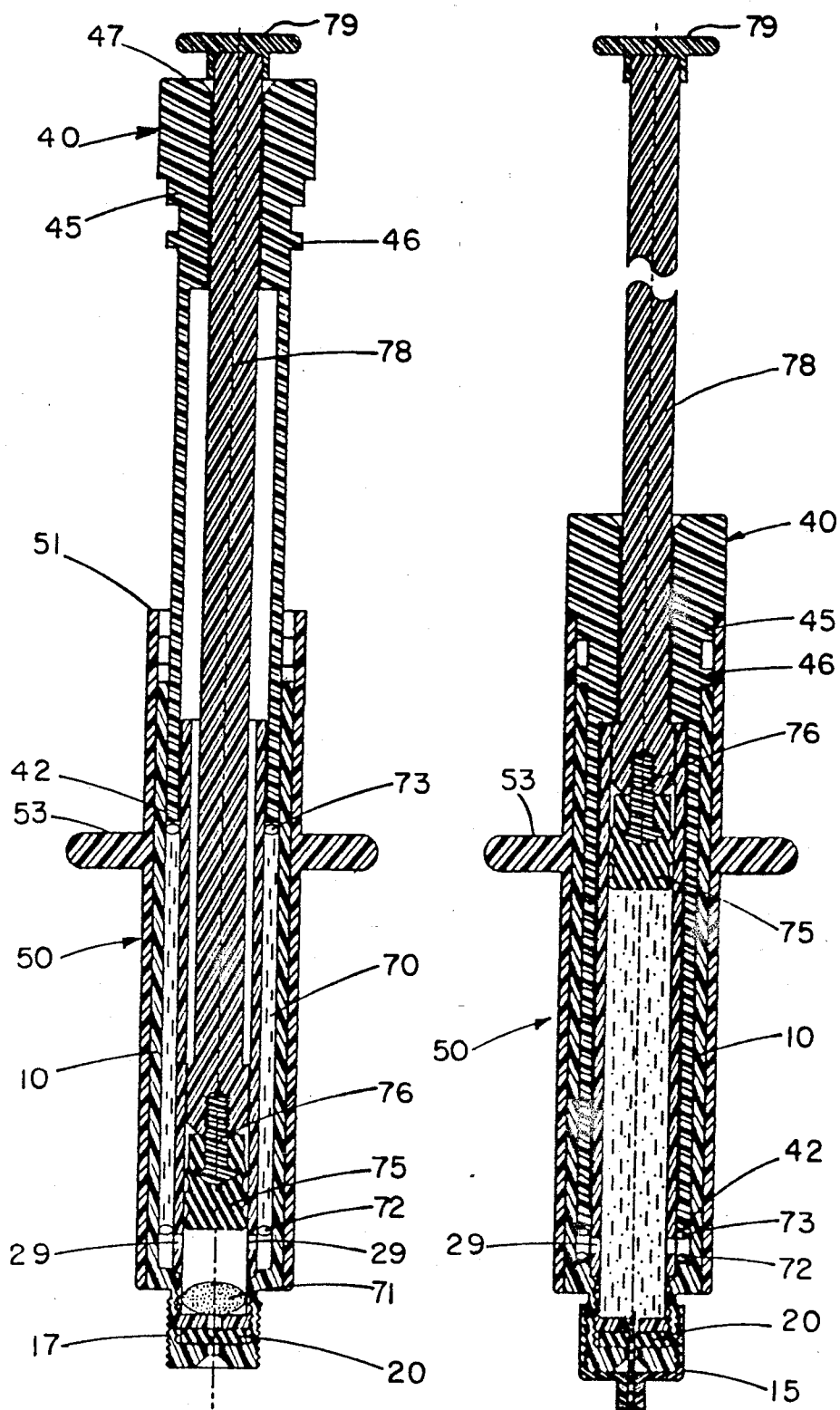
FIGS. 6A and 6B are full sectional views illustrating the FIG. 4 embodiment prior to and after mixing.
Figure 6C:
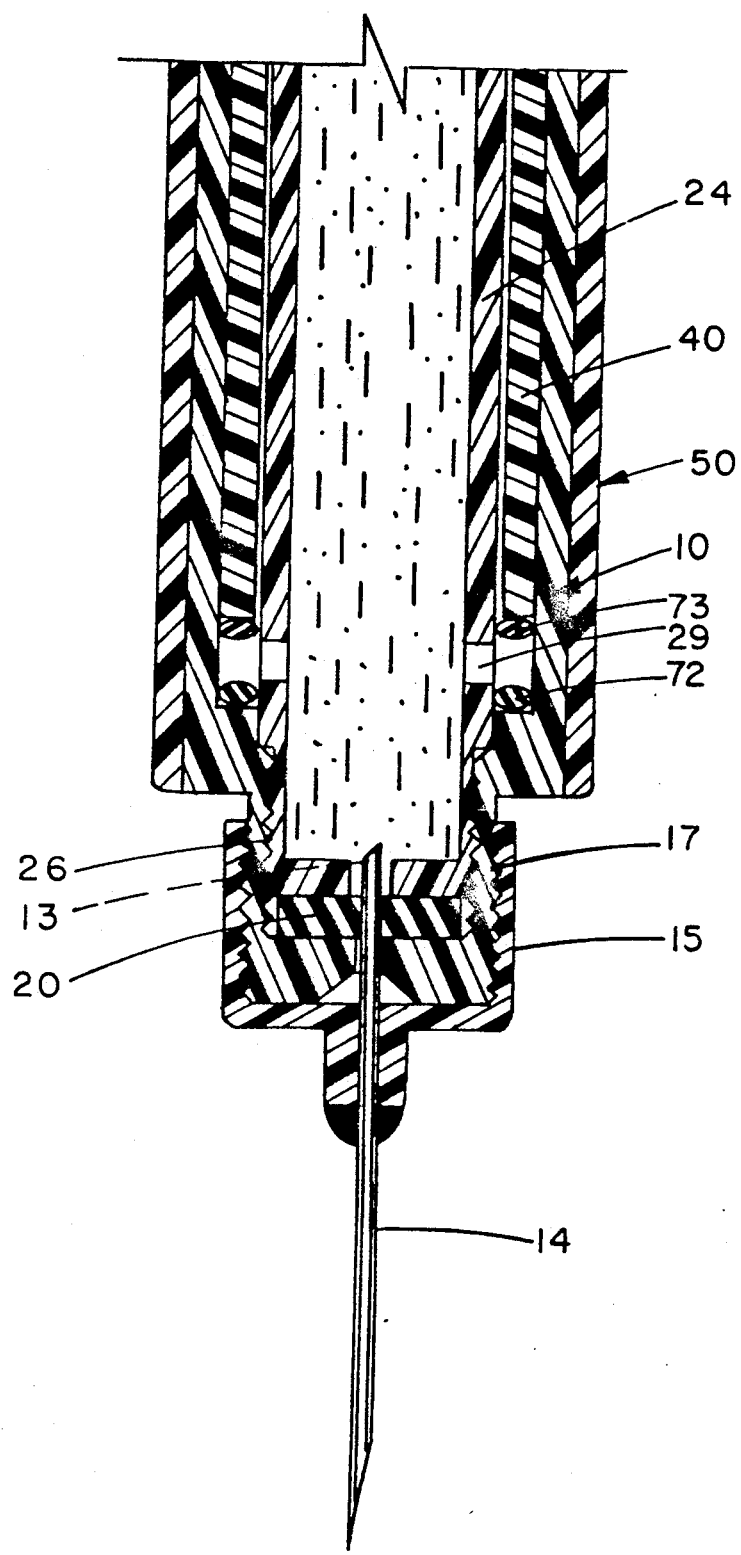
FIG. 6C is an enlarged sectional view illustrating the final position of the sealing bands after mixing.
Figure 6D:
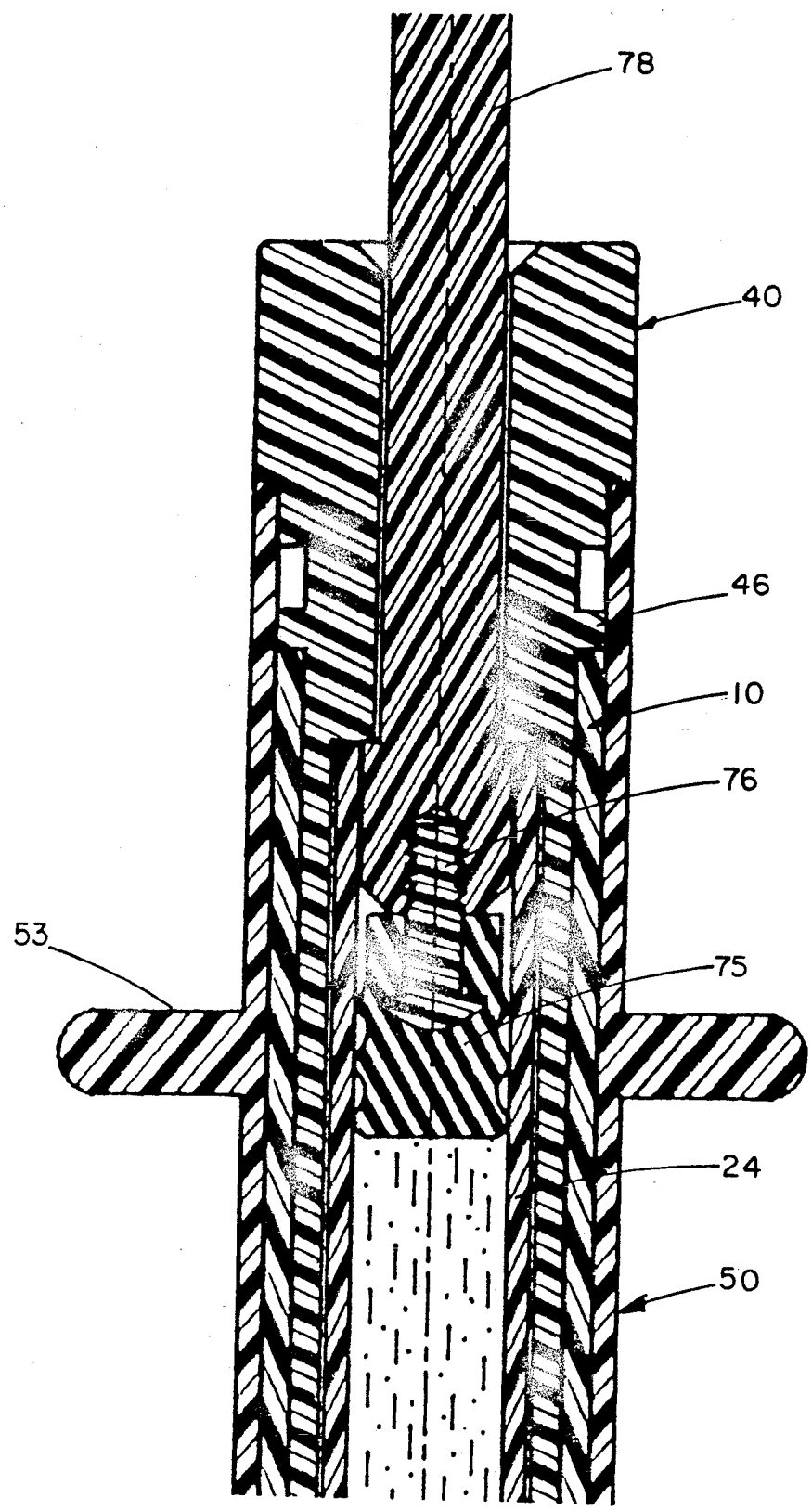
FIG. 6D is an enlarged view illustrating the detent mechanism after mixing.

Since the driving member 50 is bonded to the first housing element 10, relative motion is provided by grasping the ledge 53 with two fingers, and pushing on the upper edge 47 of band driving sleeve 40. This drives the sleeve 40 downwardly. Thereafter, sleeve 40 can be rotated by grasping the upper portion thereof and twisting it while grasping the member 50 to lock pin 46 into slot 19. The position of the O rings 72, 73 after the two components have been thoroughly mixed is best shown in FIG. 6C; while the locking arrangement provided by pin 46 and slot 19 is best illustrated in FIG. 6D. After mixing of the two components, the syringe cap 15 is installed and the pharmaceutical may be expelled by grasping ledge 53 between two fingers and pushing down on plunger cap 79 with the thumb.

While the above provides a full and complete disclosure of the preferred embodiments of the invention, various modifications, alternate constructions and equivalents may be employed as desired. For example, other flow communication arrangements other than simple aperture 29 may be employed to provide fluid communication between the annular volume and the interior of second housing 24, e.g., slots, valving arrangements and the like. Further, other detent mechanisms, such as J-shaped hooks, may be used in place of pin 46. Therefore, the above description and illustrations should not be construed as limiting the invention, which is defined by the appended claims. Therefore, the above should not be construed as limiting the invention, which is defined by the appended claims.

What is claimed is:

1. A component mixing syringe for use in mixing a first liquid component with a second component prior to use, said syringe comprising:
   a first housing having a seal end and a second end;
   a septum located at said seal end of said first housing;
   a second housing received within said first housing and forming an annular space therewith, said second housing having a first end in sealing engagement with said seal end of said first housing, and a second end, and at least one aperture therethrough adjacent said first end to provide fluid communication between said annular volume and the interior of said second housing;
   first and second sealing bands slidably received about said second housing and mutually spaced therealong, both of said sealing bands being initially positioned above said aperture to form an annular volume for the first liquid component;
   a band driving sleeve slidably received about said second housing and located partially within said first housing, said band driving sleeve having a first end positioned adjacent the upper one of said mutually spaced bands, and a second end;
   a plunger having a seal end received within said second housing to form an enclosed volume for the second component; and
   means for enabling said band driving sleeve to be translated toward said seal end of said first housing to drive said upper one of said mutually spaced sealing bands toward said aperture, thereby causing said first liquid component to force the lower one of said sealing bands to slide below said aperture permitting said first liquid component to mix with the second component within the interior of said second housing.

2. The invention of claim 1 wherein said sealing bands are O rings.

3. The invention of claim 1 wherein said sealing bands have a rectangular cross-section.

4. The invention of claim 1 wherein said septum is captured between the seal end of the first housing and the first end of said second housing.

5. The invention of claim 1 wherein said seal end of said first housing has an externally threaded portion for removably receiving a syringe needle/cap assembly.

6. The invention of claim 1 wherein said enabling means comprises a driving member slidably received about said first housing and having a first portion coupled to said band driving sleeve, and a second end, said second end of said driving member being initially axially spaced from said seal end of said first housing and engageable therewith after a selected amount of axial travel to provide a limit stop.

7. The invention of claim 1 wherein said enabling means comprises a shield member disposed about said first housing and secured thereto, said shield member having a grasping ledge formed along the periphery thereof to promote manual translation of said band driving sleeve axially of said first housing.

8. The invention of claim 1 wherein said band driving sleeve and said first housing are provided with complementary detent portions which engage when said band driving sleeve has been translated by a predetermined axial amount.

9. The invention of claim 8 wherein said complementary detent portions include at least one slot formed adjacent the second end of said first housing and a pin formed adjacent the second end of said band driving sleeve.

* * * * *